United States Patent [19]
Raditsch et al.

[11] Patent Number: 6,060,300
[45] Date of Patent: May 9, 2000

[54] THROMBIN MUTEINS AS ANTIDOTES FOR THROMBIN INHIBITORS

[75] Inventors: Martin Raditsch, Dossenheim; Thomas Friedrich, Darmstadt; Claus Bollschweiler, Heidelberg; Martin Schmidt, Bensheim; Hans Wolfgang Höffken, Ludwigshafen; Jürgen Schweden; Klaus Rübsamen, both of Neustadt, all of Germany

[73] Assignee: BASF Aktiengesellschaft, Ludwigshafen, Germany

[21] Appl. No.: 09/117,708

[22] PCT Filed: Feb. 11, 1997

[86] PCT No.: PCT/EP97/00612

§ 371 Date: Aug. 4, 1998

§ 102(e) Date: Aug. 4, 1998

[87] PCT Pub. No.: WO97/29198

PCT Pub. Date: Aug. 14, 1997

[30] Foreign Application Priority Data

Feb. 12, 1996 [DE] Germany .............. 196 05 126

[51] Int. Cl.[7] .............. C12N 9/74; A61K 38/48; A61K 38/43; C07K 1/00; C07H 21/02
[52] U.S. Cl. ............ 435/214; 424/94.64; 424/94.1; 530/384; 530/350; 536/23.1
[58] Field of Search ............... 424/94.64, 94.1; 435/214; 530/381, 350; 536/23.1

[56] References Cited

FOREIGN PATENT DOCUMENTS

93/15757  8/1993  WIPO .

OTHER PUBLICATIONS

Database Medline, No. 96053644.
Identification and Characterization of Mutant Thrombins, Henriksen, 312–340.
Biochemistry 1991, 30, 6392–6397, Stone et al.

*Primary Examiner*—W. Gray Jones
*Assistant Examiner*—Holly Schnizer
*Attorney, Agent, or Firm*—Keil & Weinkauf

[57] ABSTRACT

The invention concerns thrombin muteins which have the following differences in their sequences as compared with natural thrombin: (a) the exchange of a Gly after Ala, the Gly being in the sequence environment Tyr-Gly-Phe and having position 558 in natural human thrombin (SEQ ID No. 14); (b) at least one exchange or deletion of the following radicals: (b1) His, located in the sequence environment Ala-His-Cys and having position 363 in natural human thrombin (SEQ ID No. 14); (b2) Asp, located in the sequence environment Arg-Asp-Ile and having position 419 in natural human thrombin (SEQ ID No. 14); (b3) Ser, located in the sequence environment Asp-Ser-Gly and having position 525 in natural human thrombin (SEQ ID No. 14). The invention further concerns the use of these muteins as antidotes.

12 Claims, 3 Drawing Sheets

THROMBIN MUTEINS AS ANTIDOTES FOR THROMBIN INHIBITORS

BACKGROUND OF THE INVENTION

The present invention relates to novel thrombin muteins, to their preparation and to their use as antidote for thrombin inhibitors.

Anticoagulants which act according to the principle of direct thrombin inhibition are becoming increasingly important for anti-thrombotic therapy. An obligatory precondition for wide use of anticoagulants is the possibility of neutralizing the effect in cases of overdosage, where breakdown is impaired or excretion is slowed, in order in this way to suppress the hemorrhagic side effects which then threaten, such as bleeding in the region of the peritoneum, the pericardium and the pleura. Whereas highly effective antidotes are available for heparin in the form of protamine sulfate, polylysine and platelet factor 4, at present there is no suitable antidote for use in humans to neutralize thrombin inhibitors.

Various antidote principles are described in the literature. Fareed suggests activated plasma fractions, such as autoplex products or FEIBA, as principle for neutralizing hirudin: however, because of the activity resembling thromboplastin they are not suitable for neutralization. (Fareed, Fed Proc 3 (1989) A 328; Walenga Sem. Thromb. Hemost. 15 (1989) 316–333).

Markwardt (Thrombosis Research 74 (1994) 1–23) describes the use of thrombin and thrombin derivatives. Examples thereof are +thrombin, thrombin-2-macroglobulin complexes and meizothrombin. The use of chemically inactivated thrombins such as DFP-thrombin or benzoyl-thrombin for neutralizing hirudin is also described (Markwardt, Pharmazie, 44 (1989) 648–649).

However, these products are unsuitable as antidotes for use in humans because of the coagulation activity and of the affinity for hirudin which is up to 1000 times lower (F. Doyle in Methods Enzymol; Vol. 222, pp 299 et seq., Moriata in Methods Enzymol; Vol 80, pp 303 et seq., Stone et al. Biochemistry 26 (1987) 4617–4624, Markwardt, Pharmazie, 44 (1989) 648–649).

Human prothrombin is known and is described in Friezner et al. (Biochemistry, 22 (1983) 2087–2097). The amino-acid sequence of human prothrombin is also indicated in SEQ ID NO:14. Various ways of numbering the human thrombin sequence are to be found in the literature, which is why the way of numbering shown in SEQ ID NO:14 is used hereinafter unless indicated otherwise.

A genetically engineered, enzymatically inactive thrombin is described by Lentz et al. (JBC 266, No. 15, 9598–9604). In this, replacement of the serine residue, which is necessary for the catalysis, at position 205 (position 525 in SEQ ID NO:14) by alanine results in an enzymatically inactive thrombin variant which has no cleavage activity on synthetic substrates and the natural substrate fibrinogen (Lentz et al., JBC 266, No. 15, 9598–9604) but has a lower binding affinity for the thrombin inhibitor danzylarginine-N-(3-ethyl-1,5-pentanediyl)amide.

Studies by Stone et al. (Biochemistry 30, 6392–6397) have disclosed the natural thrombin variant quick II. Quick II thrombin differs from natural thrombin only at position 238 (position 558 in SEQ ID NO:14). In this case, glycine residue 238 in the natural thrombin is mutated to the hydrophobic residue valine. This minor replacement in the P1 pocket of the enzyme leads to a distinctly reduced rate of cleavage of fibrinogen (2% of the original activity) and, at the same time, to a drastic reduction in the binding both of low molecular weight substrates and of hirudin. Stone showed that the binding constant of the mutein for hirudin has become worse by a factor of more than 1000 and explains this result both by steric blocking of the binding cavity and by a conformal reorganization of the environment of the active center.

Thrombin muteins disclosed to date are unsuitable as antidote for thrombin inhibitors because either their affinity for the thrombin inhibitor is too low or their binding and enzymatic activity on fibrinogen are too high.

BRIEF SUMMARY OF THE INVENTION

It is an object of the present invention to provide novel thrombin muteins which are substantially enzymatically inactive, bind well to the thrombin inhibitor and, at the same time, bind to the natural substrate fibrinogen with a lower affinity than unmodified thrombin.

BRIEF DESCRIPTION OF THE DRAWINGS

FIG. 3: (A and B) Neutralization of PEG-hirudin in dogs.

DETAILED DESCRIPTION OF THE INVENTION

We have found that this object is achieved by thrombin muteins which have the following differences in sequence compared with natural thrombin (a) replacement of a Gly by Ala, the Gly being located in the sequence environment Tyr-Gly-Phe and occupying position 558 in natural human prothrombin (SEQ ID NO:14);

(b) at least one replacement or deletion of the following residues (b1) His which is located in the sequence environment Ala-His-Cys and occupies position 363 in natural human prothrombin (SEQ ID NO:14);

(b2) Asp which is located in the sequence environment Arg-Asp-Ile and occupies position 419 in natural human prothrombin (SEQ ID NO:14);

(b3) Ser which is located in the sequence environment Asp-Ser-Gly and occupies position 241 in natural human thrombin (SEQ ID NO:14);

The novel thrombin muteins can be prepared starting from known natural thrombins such as thrombin from humans and other mammals, for example primates, cattle, pigs, dogs, cats, mice, rats. By natural thrombin is meant a polypeptide sequence which has thrombin activity and occurs naturally in an organism.

Thrombin muteins mean not only disulfide-linked two-chain molecules (A and B chains) but also molecules in single-chain form such as prethrombin or proteins which consist only of the B chain or parts of the B chain, preferably of N- and/or C-terminally truncated B chains. It is crucial for the thrombin muteins according to the invention that the activity in respect of thrombin inhibitor binding is present.

The thrombin muteins according to the invention can also be prepared starting from known products of thrombin proteolysis, for example β-thrombin, γ-thrombin, ω-thrombin or else thrombin precursors such as prothrombin, prothrombin intermediate or else meizothrombins, which can then be converted where appropriate by suitable cleavage methods, for example using factor Xa, fractions of the venom from Echis carinatus or else Oxyranus scutellatus snakes into the active thrombin molecules.

The thrombin muteins according to the invention are suitable for neutralizing hirudin, hirudin derivatives or other thrombin inhibitors.

Preparation by genetic engineering is preferred, in which an appropriate gene for the thrombin mutein is prepared and this gene is expressed in a suitable host organism.

The novel thrombin muteins have at least two differences in sequence from natural thrombin, the first difference being a replacement of a glycine residue by an alanine residue. The position of the replacement depends on the origin of the natural initial thrombin. It is, however, the glycine position located in the sequence environment Tyr-Gly-Phe and occupying position 558 in natural human prothrombin (SEQ ID NO:14).

The second difference in sequence is either a replacement or a deletion of an amino-acid residue at one of the three positions (His, Asp, Ser) which form the catalytic triad of the protease thrombin. In natural human prothrombin (SEQ ID NO:14), these positions are 363 for His, 419 for Asp and 525 for Ser. In other non-human thrombins, these positions may be displaced somewhat depending on the total length of the molecule. The sequence environment, ie. the amino-acid residues in front of and behind the appropriate amino acid, is conserved in the thrombins, however, and it is therefore possible easily to establish the exact position of the appropriate amino-acid residue on the basis of the sequence environment.

The thrombin muteins according to the invention may also have several alterations (deletions or substitutions) on the catalytic triad. Thrombin muteins which have a single alteration on the catalytic triad are preferred.

Preferred alterations are those involving substitutions of the amino acids in the catalytic triad. The histidine residue is preferably substituted by polar or hydrophobic amino acids, in particular by Phe, Tyr, Ala or Val. The aspartate residue is preferably substituted by other polar amino acids, for example Gln or Asn.

Particularly preferred thrombin muteins are those in which the serine residue is altered, in particular the serine is substituted by amino acids which have no hydroxyl functionality, in particular those having a similar volume to Ser. Substitution of Ser by Ala is very particularly preferred.

The activity of these thrombin muteins can be further improved by producing other alterations into the molecule. Thus, for example, it is conceivable further to improve the proteolytic stability in order, for example, to make a longer in vivo duration of action possible. For this it is possible, for example, to replace the basic residues Arg 393, Lys 465, Arg 390 or Arg 382 (SEQ ID NO:14), by another non-basic amino acid.

The invention further relates to nucleic acid sequences, in particular DNA sequences, which code for the thrombin muteins described. These can easily be determined by translating the polypeptide sequence back into the corresponding DNA sequence in accordance with the genetic code. Codons preferably used are those which lead to good expression in the required host organism.

The nucleic acid sequence can be prepared either by site-specific mutagenesis starting from the natural thrombin gene sequence or else completely synthetically by DNA synthesis.

The thrombin muteins according to the invention are particularly suitable as antidote for thrombin inhibitors such as hirudins, hirudin derivatives and low molecular weight thrombin inhibitors.

Hirudins are proteins which were originally isolated from leeches, consist of 65 amino acids and have extremely high affinity for thrombin (ki=$10^{-12}$ mol/l) and excellent selectivity for thrombin. Hirudins have been shown to be active both in animal experiments and in humans. Besides the originally isolated hirudins there are also numerous hirudin muteins and isohirudins whose sequences show modifications compared with natural hirudin. By hirudins are therefore meant not only natural hirudins but also hirudins which have one or more modifications in the sequence relative to the hirudin from Hirudo medicinalis and which have at least equally high affinity for thrombin.

Hirudins can easily be obtained by genetic engineering methods. Their half-life in humans is about 45 minutes.

Also known are hirudin derivatives where the chemical modification has modified the pharmacokinetics of hirudin. Markwardt describes conjugates of dextran and hirudin with an extended duration of action. EP 345616, EP 502962 and EP 557199 disclose long-acting polymer conjugates. WO 9515183 describes long-acting hydrophobic Hirudin derivatives. Depot forms and long-acting Hirudin dimers (WO 9504823) are likewise known. Further thrombin inhibitors are low molecular weight thrombin inhibitors disclosed, for example, in EP 236164, DE 2801478, EP 293881 or EP 185390.

Further thrombin inhibitors are recombinant desulfatohirudins, hirudin muteins, polymer-modified hirudins such as dextran-hirudins, PEG-hirudins, hydrophobic hirudin derivatives, and hirudin muteins with an extended duration of action. The novel thrombins can furthermore be employed to antagonize hirudsins, truncated hirudins and hirudin analogs derived from hirudin and partial sequences thereof, such as hirulogs or C-terminal hirudin peptides. It is also possible to neutralize other thrombin-inhibitory peptides, for example described from blood-sucking organisms and employed for therapy after genetic engineering preparation, such as rhodniin; infestin.

Examples of thrombin inhibitors which can be neutralized are also synthetic, preferably low molecular weight, thrombin inhibitors such as derivatives of the tripeptide D-Phe-Pro-Arg, NAPAP, boronic acid derivatives, arginals or benzamidine derivatives. The use according to the invention as antidote is applicable to all the abovementioned thrombin inhibitors.

The thrombin muteins according to the invention neutralize the thrombin inhibitors better than the principles hitherto described for neutralizing thrombin inhibitors. The thrombins according to the invention are safe on use, even in the event of overdosage, and therefore make it possible in emergency situations to neutralize the thrombin inhibitors rapidly and effectively.

The thrombin muteins according to the invention are provided in a form suitable for parenteral administration, ie. for subcutaneous, intramuscular or intravenous administration. Intravenous administration is preferred. The thrombin muteins according to the invention can, where appropriate, also be administered as continuous infusion. The amount of inactive thrombin to be administered depends, for example, on the extent of the overdosage, the body weight and the chosen administration form. The extent of the overdosage can be determined by a skilled worker before or else during the administration of the thrombin by suitable tests.

The thrombin muteins according to the invention can be prepared by genetic engineering methods. Genetic engineering preparation of a precursor form of the thrombin mutein (analogous to prothrombin), from which the thrombin mutein can be liberated by proteolytic activation, is preferred.

Another preferred form of preparation, especially for thrombin muteins consisting only of the B chain, is expression of the gene for the B chain modified according to the invention in microorganisms, preferably in bacteria such as E. coli.

The resulting expression product must, where appropriate, be renatured by methods familiar to the skilled worker in order to obtain an active thrombin mutein molecule. On expression of the B chain in bacteria it has also emerged that it is advantageous to replace the Cys residue, which in natural human thrombin contributes to the S-S linkage, by another amino acid residue, eg. Ser or Ala.

The following examples serve to illustrate the invention further but without restricting it.

Prothrombin was cloned from a human liver cDNA bank in accordance with the publication by Degen et al (Biochemie 22 (1983) 2087–97).

The muteins according to the invention were prepared by targeted mutagenesis in the thrombin part.

EXAMPLE 1

Preparation of Ala 558-Prothrombin

The codon GGC for the amino acid glycine in position 558 (SEQ ID NO:14) of human prothrombin was mutated to the codon GCC for Ala by targeted mutagenesis.

To do this, the oligonucleotide SEQ ID NO: 5 was synthesized in the sense direction of the gene, and the oligonucleotide SEQ ID NO: 6, which is complementary thereto was synthesized in the antisense direction, with the appropriate nucleotide exchange. The oligonucleotide SEQ ID NO: 1 was synthesized in the sense direction in accordance with the 5' end of the prothrombin gene. The sequence for the Eco R1 restriction cleavage site was additionally attached to the 5' end thereof. The oligonucleotide SEQ ID NO: 2 was synthesized in the antisense direction in accordance with the 3' end of the prothrombin gene, and the sequence for the Eco R1 restriction cleavage site was likewise attached to the 5' end thereof.

50 ng of the human prothrombin cDNA as template and 50 pmol each of the oligos SEQ ID NO: 5 and SEQ ID NO: 2 were used after addition of 2 nM dNTPs, polymerase buffer and Pfu polymerase (Stratagene) to carry out a PCR reaction with 35 cycles each of 1 min at 94° C., 2 min at 55° C. and 3 min at 72° C. Correspondingly, a second PCR was carried out with the same template and the oligos SEQ ID NO: 6 and SEQ ID NO: 1. The two DNA fragments produced in this way were purified by a standard protocol (PCR purification kit, Quiagen, Hilden). 0.1 pmol of each of the two fragments were mixed, denatured by heating at 95° C. for 5 min and kept at room temperature for 1 h for renaturation. In order to obtain a complete DNA double strand, 2 nM dNTPs, polymerase buffer and Pfu polymerase were added and then 10 cycles were carried out each for 1 min at 94° C. and 5 min at 72° C. To amplify the full-length fragment, 50 pmol of each of the outer oligos SEQ ID NO: 1 and SEQ ID NO: 2 were added and, after adding Pfu polymerase once again, another PCR was carried out with 35 cycles each of 1 min at 94° C., 2 min at 55° C. and 3 min at 72° C. The mutated prothrombin cDNA which had been prepared in this way with replacement of Gly by Ala in position 558 was purified by the standard protocol, then cut with the restriction endonuclease Eco R1 and cloned with a T4 ligase by a standard protocol into the vector pUC 18 (Pharmacia Biotech Europe GmbH, Freiburg) which had likewise been cut with Eco R1. The DNA was sequenced as a check.

EXAMPLE 2

Preparation of Ala 525, Ala 558 Prothrombin

Targeted mutagenesis was carried out to mutate the codon AGT for Ser in position 525 (SEQ ID NO:14) of human prothrombin to the codon CGT for Ala and the codon GGC for Gly in position 558 (SEQ ID NO:14) to the codon GCC for Ala.

To do this, a PCR was carried out on the basis of the prothrombin mutein DNA from Example 1 and the oligo SEQ ID NO: 3 with the appropriate nucleotide replacement for Ala in position 525 in the sense direction and with the oligo SEQ ID NO: 2 (3'-end prothrombin). The experimental conditions corresponded to those in Example 1. A second PCR was carried out with the oligo SEQ ID NO: 4 which is complementary to SEQ ID NO: 3, and with oligo SEQ ID NO: 1 (5'-end prothrombin). The DNA fragments obtained in this way were denatured, hybridized and filled in to give the double strand, and then another PCR with the outer oligos SEQ ID NO: 1 and SEQ ID NO: 2 was carried out in accordance with Example 1.

The prothombin mutein cDNA prepared in this way was purified, then cut with Eco R1, cloned into the vector pUC 18 and sequenced as a check.

EXAMPLE 3

Preparation of Ala 363, Ala 558 Prothrombin

Targeted mutagenesis was carried out to mutate the codon AGT for His in position 363 (SEQ ID NO:14) of human prothrombin to the codon GCA for Ala and the codon GGC for Gly in position 558 (SEQ ID NO:14) to the codon GCC for Ala.

To do this, a PCR was carried out on the basis of the prothrombin mutein DNA from Example 1 and the oligo SEQ ID NO:10 with the appropriate nucleotide replacement for Ala in position 563 in the sense direction, and with the oligo SEQ ID NO: 2 (3'-end prothrombin). The experimental conditions corresponded to those in Example 1. A second PCR was carried out with the oligo SEQ ID NO: 11 which is complementary to SEQ ID NO: 10, and with the oligo SEQ ID NO: 1 (5'-end prothrombin). The DNA fragments obtained in this way were denatured, hybridized and filled in to give the double strand, and then another PCR was carried out with the outer oligos SEQ ID NO: 1 and SEQ ID NO: 2 in accordance with Example 1.

The prothrombin mutein cDNA prepared in this way was purified, then cut with Eco R1, cloned into the vector pUC 18 and sequenced as a check.

EXAMPLE 4

Preparation of Asn 419, Ala 558 Prothrombin

Targeted mutagenesis was carried out to mutate the codon GAC for Asp in position 419 (SEQ ID NO:14) of human prothrombin to the codon CGA for Asn and the codon GGC for Gly in position 558 (SEQ ID NO:14) to the codon GCC for Ala.

To do this, a PCR was carried out on the basis of the prothrombin mutein DNA from Example 1 and the oligo SEQ ID NO: 12 with the appropriate nucleotide replacement for Asn in position 419 in the sense direction and with the oligo SEQ ID NO: 2 (3'-end prothrombin). The experimental conditions corresponded to those in Example 1. A second PCR was carried out with the oligo SEQ ID NO: 13 which is complementary to SEQ ID NO: 12, and with oligo SEQ ID NO: 1 (5'-end prothrombin). The DNA fragments obtained in this way were denatured, hybridized and filled in to give the double strand, and then another PCR with the outer oligos SEQ ID NO: 1 and SEQ ID NO: 2 was carried out in accordance with Example 1.

The prothombin mutein cDNA prepared in this way was purified, then cut with Eco R1, cloned into the vector pUC 18 and sequenced as a check.

EXAMPLE 5

Preparation of Ala 525-Prothrombin

Targeted mutagenesis was carried out to mutate the codon AGT for Ser in position 525 (SEQ ID NO: 14) of human prothrombin to the codon GCT for Ala.

To do this, a PCR was carried out on the basis of the prothrombin mutein DNA and the oligo SEQ ID NO: 3 with the appropriate nucleotide replacement for Ala in position 525 in the sense direction and with the oligo SEQ ID NO: 2 (3'-end prothrombin). A second PCR was carried out with the oligo SEQ ID NO: 4 which is complementary to SEQ ID NO: 3, and with oligo SEQ ID NO: 1 (5'-end prothrombin). The DNA fragments obtained in this way were denatured, hybridized and filled in to give the double strand, and then another PCR with the outer oligos SEQ ID NO: 1 and SEQ ID NO: 2 was carried out.

The prothrombin mutein cDNA prepared in this way was purified, then cut with Eco R1, cloned into the vector pUC 18 and sequenced as a check.

EXAMPLE 6

Construction of Expression Vectors for Human Prothrombin Muteins

For secretory recombinant expression in CHO mammalian cells, the secretion leader sequence of the human tPA gene was attached at the 5' ends of the mutated prothrombin cDNAs (see Example 1 to 5) (Pennica et al., Nature 301 (1983) 214–221). Starting from a tPA cDNA, PCR-based amplification of the tPA secretion leader cDNA was carried out with the synthetic oligonucleotides SEQ ID NO: 9 (5' end of the tPA leader and Eco R1 sites) and SEQ ID NO: 8 (3' end of tPA leader, 5' end of prothrombin). Each of the mutated prothrombin mutein fragments was amplified using the oligo SEQ ID NO: 7 which is complementary to SEQ ID NO: 8, and SEQ ID NO: 2. The tPA leader fragments were added to the relevant prothrombin mutein fragments. The mixtures were denatured, hybridized filled in to give the double strand, and the relevant tPA leader prothrombin mutein DNAs were prepared with another PCR using the oligonucleotides SEQ ID NO: 9 and SEQ ID NO: 2. These were cut with Eco R1, cloned in pUC 18 and sequenced as a check.

For expression in CHO cells, these DNAs were cut out of the pUC 18 vectors with Eco R1, isolated and inserted into the Eco R1 cleavage site of the vector pc DNA3 neo (Invitrogen, San Diego, U.S.A.). Transcription of the prothrombin cDNA is under the control of the strong cytomegalovirus promoter in this vector.

Selection for transfected cells is carried out by means of the neomycin-resistance gene which is located in the plasmid and which permits only G 418-resistant colonies to grow.

Before the transfection, the appropriate DNAs intended for expression in CHO cells were linearized with the restriction enzyme PvuI, precipitated and taken up in 10 mM Tris buffer (pH 8.5) under sterile conditions.

EXAMPLE 7

Expression of Prothrombin Muteins in Mammalian Cells

The DNA of the expression vectors was transfected into mammalian cells using lipofectamine (from Gibco; Life Technologies GmbH; Dieselstraße 5, 76334 Eggenstein, Germany; No. 530-8324SA). The cells used were CHO-K1 (ATCC CCL 61); 293 (ATCC CRL 1573).

$2 \times 10^5$ cells/ml were introduced in 3 ml of growth medium into each well of a 6-well culture plate. The transfection was carried out the next day. For this, the cells were washed once with serum-free medium. The transfection with lipofectamine was carried out in accordance with the instructions of the manufacturer Gibco (Focus 15 (1993) 73–78). Each well contained 1 µg of DNA and 6 µl of lipofectamine which were introduced in a total of 1000 µl of serum-free cell culture medium. After incubation at 37° C. for 6 hours, the transfection medium was aspirated off and the cells were incubated with normal growth medium (including fetal calf serum, FCS) overnight.

EXAMPLE 8

Transient expression of prothrombin muteins in 293 cells 293 cells are kept in DMEM (Gibco No. 41965)+10% FCS (Biowhittaker No. 14601B).

The transfection was carried out as described above. In this case, to increase expression, cotransfection was carried out with the plasmid pAdVantage (from Promega No. E1711). 0.2 µg of the pAdVantage DNA and 0.8 µg of the DNA for the particular prothrombin mutein in the expression vector pcDNA3 were transfected as described above. On the first day after the transfection, the serum-containing medium was aspirated off and replaced by serum-free medium (without phenol red). On the third day after the transfection, the cell culture supernatant was removed and stored at −20° C. until assayed.

EXAMPLE 9

Stable Expression of Prothrombin Muteins in CHO-K1 Cells

The transfection was carried out as described above. CHO cells are kept and cultured in DMEM/F12=1:1 (Gibco No. 21331–020)+10% FCS. On the first day after the transfection, the cells were split so as to be distributed from one well of a 6-well plate over 20 to 100 10 cm Petri dishes. At the same time, a start was made on selecting the recombinant cells by treatment with G418 (from Gibco, 1200 µg/ml in the medium). The resulting resistant colonies were isolated by the cloning cylinder method and, after further cultivation to reach adequate numbers of cells, investigated for expression of the appropriate thrombin muteins. This was done by aspirating off the medium from confluent cells and replacing it by fresh, serum-free medium. After fixed times, eg. after 24 hours, 48 hours, the incubated cell culture supernatant was removed and assayed for the presence of prothrombin by an ELISA.

In some cases, the resulting recombinant cells were cloned by isolation in microtiter plates to increase expression.

In order to provide sufficient amounts of the serum-free cell culture supernatant, CHO cells showing good expression were cultured to confluence in medium containing 10% FCS in various culture vessels. The cells were then washed with PBS and incubated with serum-free DMEM/F12 (DMEM: Gibco No.11880–028; F12: Gibco No.21765-029: mixture consists of equal proportions by volume). The DMEM used for these purposes was free of phenol red. The medium was changed after two and three days in order to harvest the cell culture supernatant containing prothrombin muteins. Harvesting up to 10 times from one culture vessel was possible in this way. Various harvests from different culture vessels were combined in order to retain an acceptable volume for purification.

EXAMPLE 10

Detection of Expression of Recombinant Prothrombin Muteins

Cells which express prothrombin and secrete it into the cell culture medium were assayed for the presence of the recombinant prothrombin by investigating the cell culture supernatant from confluent cells for the presence of prothrombin by means of an ELISA or after cleavage of the prothrombin for thrombin activity or thrombin antigen.

To do this, the serum-free cell culture supernatant was removed after culturing for various times. Cleavage of the prothrombin present in the cell culture supernatant was achieved using snake venom (from Sigma; cat. No. V3129). Each mixture was carried out in the following way:

388 $\mu$l of sample (serum-free cell culture supernatant or prothrombin)

63 $\mu$l of snake venom (0.2 mg /ml in $H_2O$)

50 $\mu$l of buffer (1 M NaCl; 100 mM $CaCl_2$; 200 mM Tris pH7.4)

100 $\mu$l of $H_2O$

The cleavage mixtures were incubated at room temperature for minutes.

The resulting thrombin was subsequently characterized in various assays.

EXAMPLE 11

Detection of Prothrombin Muteins and Thrombin Muteins by ELISA

The ELISA for determining prothrombin and thrombin was carried out as shown in the following scheme:

Coat microtiter plates with 0.1 ml/well anti-thrombin antibodies; 5 $\mu$g/ml 0.05 M $NaHCO_3$ pH 9.2; 16 hours/4° C.

saturate with 1% BSA/PBS; 0.3 ml/well; 0.5–1 hour/RT wash 3× with 0.05% Tween 20/PBS 11 standard 2-fold dilutions of human thrombin (Calbiochem 605195; 3.159 NIH U/mg), starting at 10 ng/ml 0.1% BSA/0.05% Tween 20/PBS; parallel dilutions of the samples to be determined; 0.1 ml/well; 2–4 hours/RT wash as above 0.1 ml/well biotinylated anti-thrombin antibody 1:200; diluted in 0.1% BSA/0.05% Tween 20/PBS; 2–4 hours/RT wash as above 0.1 ml/well streptavidin-peroxidase complex (B.M. 1089153);

diluted 1:10000 in 0.1% BSA/0.05% Tween 20/PBS; 30 minutes/RT wash as above 0.1 ml/well peroxidase substrate stop reaction with 0.1 ml/well 2M $H_2SO_4$ measure absorption at 450 nm Peroxidase substrate: mix 0.1 ml of TMB solution (42 mM TMB in DMSO) and 10 ml of substrate buffer (0.1 M Na acetate pH 4,9); then add 14.7 $\mu$l of 3% $H_2O_2$.

EXAMPLE 12

Preparation of Antibodies Against Human Thrombin

To induce polyclonal antibodies, rabbits were immunized as follow:

Day 1 200 $\mu$g of human thrombin in 0.5 ml of PBS/complete Freund's adjuvant (Sigma F5881)

Day 14 200 $\mu$g of human thrombin in 0.5 ml of PBS/incomplete Freund's adjuvant (Sigma F5506)

Day 28 200 $\mu$g of human thrombin in 0.5 ml of PBS/incomplete Freund's adjuvant Day 42 200 $\mu$g of human thrombin in 0.5 ml of PBS 7 days after the last immunization, blood was taken from the rabbits' ear vein.

The polyclonal rabbit antibodies were purified from the collected serum on protein A Sepharose (as specified by the manufacturer Pharmacia) with a yield of 65 mg of IgG/10 ml of serum. Before the biotinylation, the antibodies were dialyzed against 0.05 M $NaHCO_3$ pH 9.0 (2×2 l), and then 200 $\mu$l of biotin X NHS ester (Calbiochem 203189; 1 mg /ml $H_2$) were added per 600 $\mu$l of antibodies (2.4 mg /ml) and shaken at RT for 2 hours. Finally, the mixture was dialyzed against PBS 3 times.

A sandwich ELISA was constructed using the antibodies obtained:

Coat microtiter plates with 0.1 ml/well anti-thrombin Ab 5 $\mu$g/ml in 0.05 M $NaCO_3$, pH 9.2; 16 hours/4° C.

saturate with 1% BSA; 0.3 ml/well; 0.5 hour/RT wash 3× with 0.05% Tween 20/PBS 11 standard 2-fold dilutions of human thrombin (Calbiochem 605195) starting with 10 ng/ml 0.1% BSA/PBS/0.05% Tween 20; parallel dilutions of the samples to be determined; 0.1 ml/well; 2 hours/RT wash as above 0.1 ml/well biotinylated anti-thrombin Ab diluted 1:200 in 1% BSA/PBS/0.05% Tween 20; 2 hours/RT wash as above 0.1 ml/well streptavidin-peroxidase complex (B.M. 1089153), diluted 1:10000 in 0.1% BSA/PBS/0.05% Tween 20; 30 minutes/RT 0.1 ml/well peroxidase substrate stop reaction with 0.1 ml/well 2M $H_2SO_4$ measure absorption (OD) at 450 nm.

Figure 1:
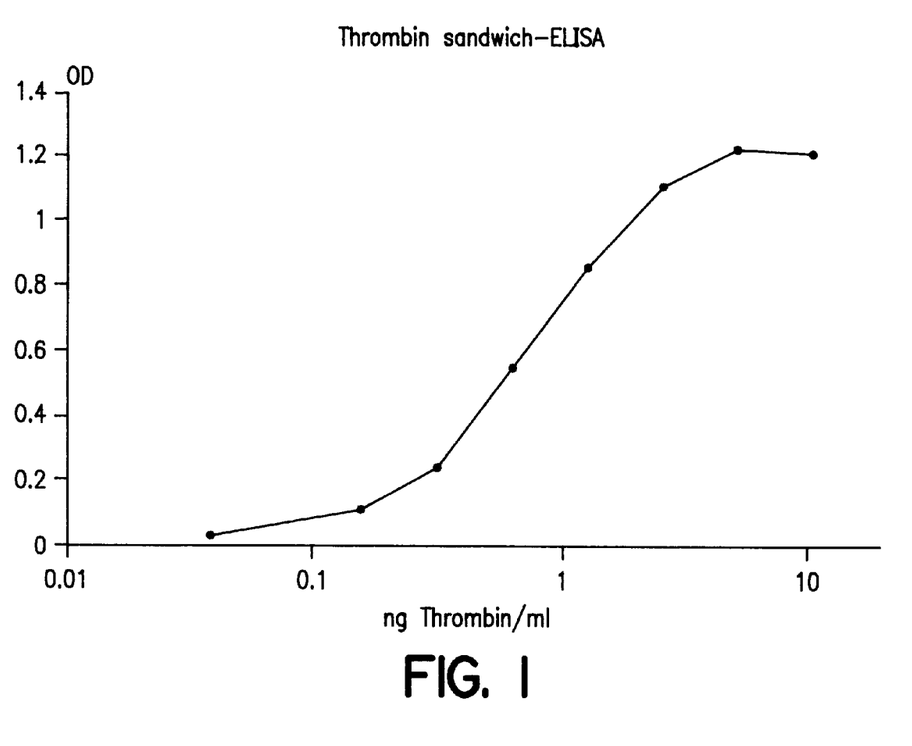
FIG. 1: Plot of thrombin sandwich ELISA constructed using prepared antibodies.

The absorption (OD) is plotted against the thrombin concentration in FIG. 1.

Peroxidase substrate: Mix 0.1 ml of TMB solution (42 mM in DMSO) and 10 ml of substrate buffer (0.1 M Na acetate pH 4.9); then add 14.7 $\mu$g of 3% $H_2O_2$.

Detection of prothrombin muteins and thrombin muteins by ELISA.

The ELISA for determining prothrombin and thrombin was carried out as shown in the following scheme:

Coat microtiter plates with 0.1 ml/well anti-thrombin antibodies; 5 µg/ml 0.05 M NaHCO$_3$, pH 9.2; 16 hours/4° C.

saturate with 1% BSA/PBS; 0.3 ml/well; 0.5–hour/RT wash 3× with 0.05% Tween 20/PBS 11 standard 2-fold dilutions of human thrombin (Calbiochem 605195; 3.159 NIH U/mg), starting at 10 ng/ml 0.1% BSA/0.05% Tween 20/PBS; parallel dilutions of the samples to be determined; 0.1 ml/well; 2–4 hours/RT wash as above 0.1 ml/well biotinylated anti-thrombin antibody 1:200; diluted in 0.1% BSA/0.05% Tween 20/PBS; 2–4 hours/RT wash as above 0.1 ml/well streptavidin-peroxidase complex (B.M. 1089153); diluted 1:10000 in 0.1% BSA/0.05% Tween 20/PBS; 30 minutes/RT wash as above 0.1 ml/well peroxidase substrate stop reaction with 0.1 ml/well 2 M H$_2$SO$_4$ measure absorption at 450 nm Peroxidase substrate: mix 0.1 ml of TMB solution (42 mM TMB in DMSO) and 10 ml of substrate buffer (0.1 M Na acetate pH 4.9); then add 14.7 µl of 3% H$_2$O$_2$.

EXAMPLE 13a

Purification of Human Thrombin from Blood Plasma

Human prothrombin was purified from citrated human plasma as described in Henrikson (Methods in Enzymology, Vol 222, pp 312–3279. The prothrombin cleavage and purification of thrombin by heparin chromatography took place as indicated in Example 14 and 15. The thrombin-containing fractions were identified by means of the chromogenic thrombin assay using S 2238 and were concentrated to 1 mg /ml by ultrafiltration and subjected to diafiltration against PBS.

Determination of thrombin activity using the chromogenic substrate S 2238

The activity of the thrombin muteins is measured from the cleavage of a tripeptide. The pipetting scheme for this purpose is as follows:

50 µl of sample (thrombin 0.5 U/ml; or cleaved prothrombin in various dilutions)

100 µof H$_2$O

50 µl of S-2238 (1 mg /ml in H$_2$O; from Chromogenix, Mölndal; Sweden).

The mixtures are incubated at 37° C. for 10–15 minutes. The absorption is then measured at a wavelength of 405 nM and the amount of thrombin is found from a calibration plot from 0.01 to 1 U/mi.

EXAMPLE 13b

Purification of Prothrombin Muteins by Anion Exchange Chromatography 35 l of the prothrombin-containing cell culture supernatant from the CHO cell culture is initially concentrated to 400 ml by ultrafiltration at 4° C. (SPS 400 Membrane, Fresenius, St. Wendel) and then subjected to diafiltration against 10 mM Tris pH 7.5 until the conductivity is 1.1 mS/cm. The desalted filtrate is then loaded onto a Q-Sepharose FF column (5 cm diameter, vol 530 ml) at a flow rate of 6 ml/min, and the column is washed with starting buffer (20 mM Tris/HCl pH 7.5) and subsequently developed with a gradient to 400 mM NaCl over 15 column volumes. The prothrombin-containing fractions are identified by ELISA. The prothrombin mutein elutes from 280 mM NaCl onwards. About 150–200 mg of protein are isolated from this column.

EXAMPLE 14

Liberation of the Thrombin Muteins from Prothrombin

The fractions from the Q-Sepharose chromatography which have been concentrated in an Amicon YM 30 (final volume 20 ml, 175 mg total protein) are dialyzed against 2 liters of 20 mM Tris/HCl pH 7.5, 100 mM NaCl and adjusted to a final concentration of 10 mM by adding 1 M CaCl 20 mM Tris pH 7.5 for the cleavage. Addition of 30 mg of venom from Oxyranus scutellatus snakes is followed by cleavage at 4° C. with stirring, and the reaction is stopped after 12 h by adding 2 ml of 20 mM EGTA solution, pH 7.5.

EXAMPLE 15

Purification of the Thrombin Muteins by Heparin Chromatography

The thrombin-containing cleavage mixture from Example 14 is subsequently loaded onto a heparin-Sepharose column (14 cm×1 cm, Pharmacia) at a flow rate of 38 cm/h. After the column has been washed with 20 ml 20 mM Na phosphate, 0.1 M NaCl pH 7.5, 0.01% Pluriol F68, it is developed with a linear gradient to 600 mM NaCl, 20 mM Na phosphate, pH 7.5, 0.01% Pluriol F68 over 150 ml. The thrombin muteins are then detected by an ELISA. The muteins elute at about 400 mM NaCl. 30–35 mg of mutein were obtained and, after addition of BSA (1 mg /ml), dialyzed against PBS, 0.01% Pluriol F68 and stored −20° C.

EXAMPLE 16

Neutralization of Hirudin in an in Vitro System

The antidote effect of the inactive recombinant thrombins on hirudin was detected in a thrombin activity assay. This was done by incubating hirudin, the thrombin mutein to be assayed, active thrombin and S-2238 together. The principle on which this assay is based is the neutralization (or competition) of hirudin by the inactive thrombin to be assayed, and the resulting higher activity of the active thrombin.

The pipetting scheme for this was as follows:

100 µl of hirudin HL20 (1.5 U/ml) or 0.1% BSA in TBS pH 7.5 and 100 µl of thrombin mutein (prepared in Example 2) were preincubated at room temperature for 5 minutes. After addition of 50 µl of active thrombin (0.5 U/ml), the reaction was started by adding 50 µl of S-2238 (1 mg /ml in H$_2$O; from Chromogenix, Mölndal; Sweden). The mixtures were incubated at 37° C. for 15 minutes. Subsequently, the absorption at a wavelength of 410 nm was measured.

Figure 2:
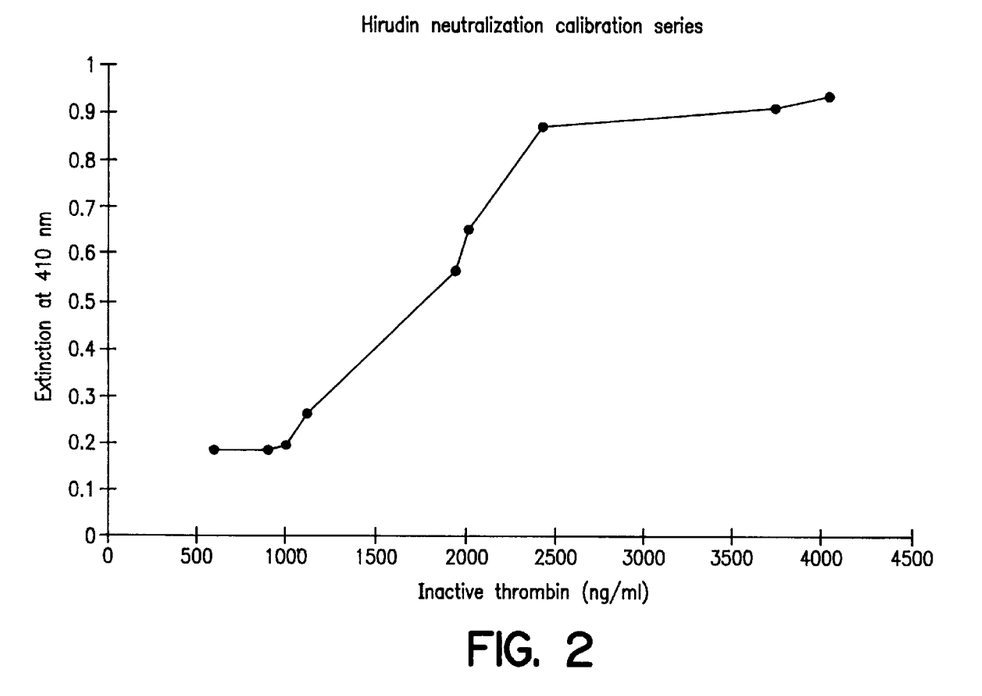
FIG. 2: Hirudin naturalization calibration series.

Neutralization of the hirudin by the inactive thrombin mutein led to an increase in absorption (FIG. 2).

EXAMPLE 17

Neutralization of PEG-Hirudin in Dogs

Beagle dogs (9.8–13.5 kg) received subcutaneous administration of PEG-hirudin at a dose of 10 mg /kg. 180 min after the PEG-hirudin injection, the thrombin mutein prepared in Example 2 (Thrombinmut #3) was administered as an intravenous infusion in a dose of 20 g/kg over 50 min. Blood samples were taken from the dogs by puncture of the brachial vein at the start of the experiment and further samples after 150 minutes over a period of up to 6 h. The plasma was obtained from the citrated blood by centrifugation at 2000 g for 20 min and was stored at −20 C. until analyzed.

The antithrombin activity in the plasma samples was determined as described by Spannagel et al., Blood Coagulation Fibrinolysis 2 (1991) 121–127. The anticoagulant activity (aPTT) was determined using the Pathromtin system (Behring).

Figure 3A:
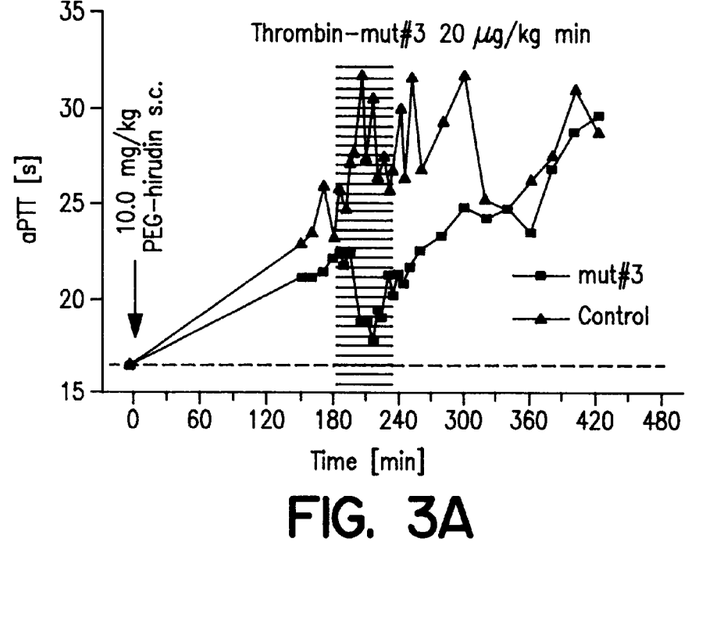
Figure 3B:
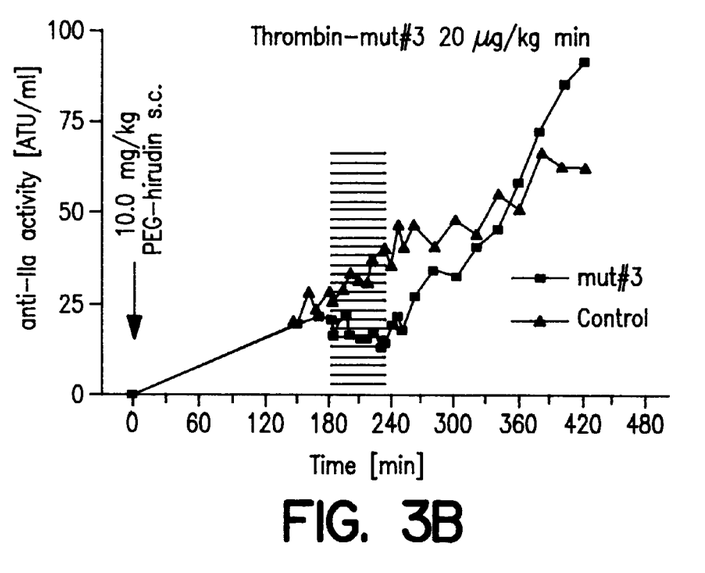

The results are summarized in FIG. 3. Whereas the antithrombin activity rose rapidly after administration of PEG-hirudin in the control animals, it was possible to prevent a rise in antithrombin activity (FIG. 3B) in the animals treated with the antidote. After completion of the antidote infusion, the PEG-hirudin plasma level rose further at a rate comparable to that in the control animals. Qualitatively the same course is also observed in the aPTT (FIG. 3A).

We claim:

1. An isolated thrombin mutein which has the following differences in sequence compared with natural thrombin
   (a) replacement of a Gly by Ala, the Gly being located in the sequence environment Tyr-Gly-Phe and occupying position 558 in natural human prothrombin (SEQ ID NO:14);
   (b) at least one replacement or deletion of the following residues
      (b1) His which is located in the sequence environment Ala-His-Cys and occupies position 363 in natural human prothrombin (SEQ ID NO:14);
      (b2) Asp which is located in the sequence environment Arg-Asp-Ile and occupies position 419 in natural human prothrombin (SEQ ID NO:14);
      (b3) Ser which is located in the sequence environment Asp-Ser-Gly and occupies position 525 in natural human prothrombin (SEQ ID NO:14).

2. An isolated thrombin mutein as defined in claim 1 which has the following differences in sequence compared with natural human prothrombin (SEQ ID NO:14)
   (a) replacement of Gly by Ala at position 558 and
   (b) at least one replacement or deletion of the following residues
      (b1) His at position 363;
      (b2) Asp at position 419;
      (b3) Ser at position 525.

3. An isolated thrombin mutein as defined in claim 2, where difference (b) in the sequence is replacement at position 525.

4. An isolated thrombin mutein as defined in claim 3, where difference (b) in the sequence is replacement of Ser by Ala.

5. A nucleic acid sequence coding for the isolated thrombin mutein of claim 1.

6. A pharmaceutical composition which is an antidote for a thrombin inhibitor, which composition comprises the isolated thrombin mutein defined in claim 1 and customary pharmaceutical auxiliaries.

7. A method for neutralizing a thrombin inhibitor in a mammal, which method comprises administering to the mammal an effective amount of the composition defined in claim 6.

8. The method of claim 7 in which the thrombin inhibitor is selected from hirudin, a hirudin mutein and a hirudin derivative.

9. The method of claim 8 in which the hirudin derivative is a hirudin which is modified with polyethylene glycol.

10. The method of claim 8 in which the thrombin inhibitor is hirudin.

11. The method of claim 8 in which the thrombin inhibitor is a hirudin mutein.

12. The method of claim 8 in which the thrombin inhibitor is a hirudin derivative.

* * * * *

```
                            SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
         (A) LENGTH: 33 base pairs
         (B) TYPE: Nucleic acid
         (C) STRANDEDNESS: single
         (D) TOPOLOGY: linear (xi) SEQUENCE DESCRIPTION: SEQ ID NO: 1:

GGGGGGGAAT TCGCCAACAC CTTCTTGGAG GAG                                       33

(2) INFORMATION FOR SEQ ID NO: 2:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 2:

GGGGGGGAAT TCCTACTCTC CAAACTGATC AAT                                       33

(2) INFORMATION FOR SEQ ID NO: 3:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 3:

GGATGCCTGT GAAGGTGACG CTGGGGGACC CTTTGTCATG                                40

(2) INFORMATION FOR SEQ ID NO: 4:

(i) SEQUENCE CHARACTERISTICS:
         (A) LENGTH: 40 base pairs
```

(B) TYPE: nucleic acid
                (C) STRANDEDNESS: single
                (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 4:

CATGACAAAG GGTCCCCCAG CGTCACCTTC ACAGGCATCC                    40

(2) INFORMATION FOR SEQ ID NO: 5:

(i) SEQUENCE CHARACTERISTICS:
                (A) LENGTH: 40 base pairs
                (B) TYPE: nucleic acid
                (C) STRANDEDNESS: single
                (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 5:

GACCGGGATG GGAAATATGC CTTCTACACA CATGTGTTCC                    40

(2) INFORMATION FOR SEQ ID NO: 6:

(i) SEQUENCE CHARACTERISTICS:
                (A) LENGTH: 40 base pairs
                (B) TYPE: nucleic acid
                (C) STRANDEDNESS: single
                (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 6:

GGAACACATG TGTGTAGAAG GCATATTTCC CATCCCGGTC                    40

(2) INFORMATION FOR SEQ ID NO: 7:

(i) SEQUENCE CHARACTERISTICS:
                (A) LENGTH: 40 base pairs
                (B) TYPE: nucleic acid
                (C) STRANDEDNESS: single
                (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 7:

TCCATGCCCG ATTCAGACGC GCCAACACCT TCTTGGAGGA                    40

(2) INFORMATION FOR SEQ ID NO: 8:

(i) SEQUENCE CHARACTERISTICS:
                (A) LENGTH: 40 base pairs
                (B) TYPE: nucleic acid
                (C) STRANDEDNESS: single
                (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 8:

TCCTCCAAGA AGGTGTTGGC GCGTCTGAAT CGGGCATGGA                          40

(2) INFORMATION FOR SEQ ID NO: 9:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 9:

GGGGGGGAAT TCGTGAAGCA ATCATGG                                       27

(2) INFORMATION FOR SEQ ID NO: 10:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 10:

CTCACCGCCG CCGCATGCCT CCTGTACCCG                                    30

(2) INFORMATION FOR SEQ ID NO: 11:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 11:

CGGGTACAGG AGGCACACGG CGGCGGTGAG                                    30

(2) INFORMATION FOR SEQ ID NO: 12:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 12:

GAACCTGGAC CGGAACATTG CCCTGAT                27

(2) INFORMATION FOR SEQ ID NO: 13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iii) ANTI-SENSE: NO (xi) SEQUENCE DESCRIPTION: SEQ ID NO: 13:

ATCAGGGCAA TGTTCCGGTC CAGGTTC                27

(2) INFORMATION FOR SEQ ID NO: 14:

(i) SEQUENCE CHARACTERISTICS:
        (A) LENGTH: 579 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 14:

Ala Asn Thr Phe Leu Glu Glu Val Arg Lys Gly Asn Leu Glu Arg Glu
1               5                  10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

-continued

```
Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
        210                 215                 220

Asp Glu Glu Gly Val Trp Cys Tyr Val Ala Gly Lys Pro Gly Asp Phe
225                     230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
                260                 265                 270

Ala Thr Ser Glu Gln Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
        290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
                340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
        370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
                420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
        450                 455                 460

Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
                500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
        530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu
        579
```